US008888762B2

(12) United States Patent
Whitman

(10) Patent No.: US 8,888,762 B2
(45) Date of Patent: *Nov. 18, 2014

(54) FLEXIBLE SHAFT EXTENDER AND METHOD OF USING SAME

(71) Applicant: Covidien LP, Mansfield, MA (US)

(72) Inventor: Michael P. Whitman, New Hope, PA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/875,640

(22) Filed: May 2, 2013

(65) Prior Publication Data

US 2013/0240596 A1    Sep. 19, 2013

Related U.S. Application Data

(63) Continuation of application No. 13/083,722, filed on Apr. 11, 2011, now Pat. No. 8,454,585, which is a (Continued)

(51) Int. Cl.
*A61B 7/00* (2006.01)
*A61B 17/068* (2006.01)

(Continued)

(52) U.S. Cl.
CPC ........... *A61B 17/068* (2013.01); *A61B 17/1626* (2013.01); *A61B 17/1631* (2013.01);

(Continued)

(58) Field of Classification Search
CPC ........... A61B 17/1631; A61B 7/32002; A61B 2017/068; A61B 2017/00477; A61B 2017/23032
USPC ................................. 606/1; 227/178.1, 180.1
See application file for complete search history.

(56) References Cited

U.S. PATENT DOCUMENTS 2,777,340 A    1/1957    Hettwer et al.
(Continued)

FOREIGN PATENT DOCUMENTS

CA    2451558 A1    1/2003
CN    102247182 A   11/2011
(Continued)

OTHER PUBLICATIONS

Extended European Search Report corresponding to EP No. 11 17 8021.9, mailed Jun. 4, 2013; (3 pp).

(Continued)

*Primary Examiner* — Linda Dvorak
*Assistant Examiner* — Kaitlyn Smith

(57) ABSTRACT

An extender for use in an electro-mechanical surgical system that includes a surgical attachment that may be detachably coupled to an electro-mechanical driver device via a flexible shaft. The extender is a substantially rigid extender that includes a proximal end that may be detachably coupled to a distal end of the flexible shaft. The extender also includes a distal end that may be detachably coupled to the surgical attachment. The extender also includes at least one rotatable drive shaft configured to engage and be secured with a respective rotatable drive shaft of the flexible shaft such that rotation of the respective rotatable drive shaft of the flexible shaft by the electro-mechanical driver device causes the at least one rotatable drive shaft of the extender to rotate, thereby rotating a complementary connector of the surgical attachment so as to operate the surgical attachment. The extender may include a memory unit and a data cable that transfers data from the memory unit to an electro-mechanical driver device. Additionally or alternatively, the extender may include a data cable that transfers data from a memory unit in the surgical attachment to the electro-mechanical driver device. Advantageously, the extender is autoclavable.

17 Claims, 22 Drawing Sheets

Related U.S. Application Data continuation of application No. 11/194,950, filed on Aug. 1, 2005, now Pat. No. 7,947,034.

(60) Provisional application No. 60/592,778, filed on Jul. 30, 2004.

(51) Int. Cl.
  *A61B 17/32* (2006.01)
  *A61B 17/04* (2006.01)
  *A61B 17/10* (2006.01)
  *A61B 17/16* (2006.01)
  *A61B 17/00* (2006.01)
  *A61B 19/00* (2006.01)

(52) U.S. Cl.
  CPC ..... *A61B 17/32002* (2013.01); *A61B 2017/003* (2013.01); *A61B 2017/00482* (2013.01); *A61B 2017/320032* (2013.01); *A61B 2019/4815* (2013.01)
  USPC .......................... 606/1; 227/178.1; 227/180.1

(56) References Cited

U.S. PATENT DOCUMENTS

| | | |
|---|---|---|
| 2,957,353 A | 10/1960 | Babacz |
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | DeEstrada |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,413,267 A | 5/1995 | Solyntjes et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,706 A | 7/1996 | Aust et al. |
| 5,542,594 A | 8/1996 | McKean et al. |
| 5,562,239 A | 10/1996 | Boiarski et al. |
| 5,653,374 A | 8/1997 | Young et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,779,130 A | 7/1998 | Alesi et al. |
| 5,782,397 A | 7/1998 | Koukline |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,017,354 A | 1/2000 | Culp et al. |
| 6,045,560 A | 4/2000 | McKean et al. |
| 6,090,123 A | 7/2000 | Culp et al. |
| 6,129,547 A | 10/2000 | Cise et al. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,077,856 B2 | 7/2006 | Whitman |
| 7,111,769 B2 | 9/2006 | Wales et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton et al. |
| 7,481,347 B2 | 1/2009 | Roy |
| 7,487,899 B2 | 2/2009 | Shelton, IV et al. |
| 7,549,564 B2 | 6/2009 | Boudreaux |
| 7,568,603 B2 | 8/2009 | Shelton, IV et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton et al. |
| 7,799,039 B2 | 9/2010 | Shelton, IV et al. |
| 7,802,712 B2 | 9/2010 | Milliman et al. |
| 7,845,537 B2 | 12/2010 | Shelton, IV et al. |
| 7,905,897 B2 | 3/2011 | Whitman et al. |

(56) References Cited

U.S. PATENT DOCUMENTS

| | | | |
|---|---|---|---|
| 7,918,230 B2 | 4/2011 | Whitman et al. | |
| 7,922,719 B2 * | 4/2011 | Ralph et al. | 606/79 |
| 7,947,034 B2 | 5/2011 | Whitman | |
| 7,951,071 B2 | 5/2011 | Whitman et al. | |
| 7,963,433 B2 | 6/2011 | Whitman et al. | |
| 7,967,178 B2 | 6/2011 | Scirica et al. | |
| 7,992,758 B2 | 8/2011 | Whitman et al. | |
| 8,016,855 B2 | 9/2011 | Whitman et al. | |
| 8,020,743 B2 | 9/2011 | Shelton, IV | |
| 8,025,199 B2 | 9/2011 | Whitman et al. | |
| 8,114,118 B2 | 2/2012 | Knodel et al. | |
| 8,157,151 B2 | 4/2012 | Ingmanson et al. | |
| 8,182,494 B1 | 5/2012 | Yencho et al. | |
| 8,186,555 B2 | 5/2012 | Shelton, IV et al. | |
| 8,220,367 B2 | 7/2012 | Hsu | |
| 8,241,322 B2 | 8/2012 | Whitman et al. | |
| 8,272,554 B2 * | 9/2012 | Whitman et al. | 227/178.1 |
| 8,292,150 B2 | 10/2012 | Bryant | |
| 8,292,888 B2 | 10/2012 | Whitman | |
| 8,342,379 B2 * | 1/2013 | Whitman et al. | 227/178.1 |
| 8,353,440 B2 * | 1/2013 | Whitman et al. | 227/180.1 |
| 8,357,144 B2 | 1/2013 | Whitman et al. | |
| 8,365,633 B2 | 2/2013 | Simaan et al. | |
| 8,365,972 B2 | 2/2013 | Aranyi et al. | |
| 8,372,057 B2 | 2/2013 | Cude et al. | |
| 8,391,957 B2 | 3/2013 | Carlson et al. | |
| 8,454,585 B2 * | 6/2013 | Whitman | 606/1 |
| 8,517,241 B2 | 8/2013 | Nicholas et al. | |
| 2002/0198554 A1 * | 12/2002 | Whitman et al. | 606/167 |
| 2003/0097133 A1 * | 5/2003 | Green et al. | 606/80 |
| 2004/0111012 A1 | 6/2004 | Whitman | |
| 2005/0187576 A1 * | 8/2005 | Whitman et al. | 606/219 |
| 2005/0214706 A1 * | 9/2005 | Harvey et al. | 433/1 |
| 2006/0142656 A1 | 6/2006 | Malackowski et al. | |
| 2006/0278680 A1 | 12/2006 | Viola et al. | |
| 2007/0023477 A1 | 2/2007 | Whitman et al. | |
| 2007/0029363 A1 | 2/2007 | Popov | |
| 2007/0055219 A1 | 3/2007 | Whitman et al. | |
| 2007/0084897 A1 | 4/2007 | Shelton, IV et al. | |
| 2007/0102472 A1 | 5/2007 | Shelton, IV | |
| 2007/0152014 A1 | 7/2007 | Gillum et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0175961 A1 | 8/2007 | Shelton et al. | |
| 2008/0029570 A1 | 2/2008 | Shelton, IV et al. | |
| 2008/0029573 A1 | 2/2008 | Shelton, IV et al. | |
| 2008/0029574 A1 | 2/2008 | Shelton, IV et al. | |
| 2008/0029575 A1 | 2/2008 | Shelton, IV et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0185419 A1 | 8/2008 | Smith et al. | |
| 2008/0208195 A1 | 8/2008 | Shores et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2009/0090763 A1 | 4/2009 | Zemlok et al. | |
| 2009/0099876 A1 | 4/2009 | Whitman | |
| 2009/0182193 A1 | 7/2009 | Whitman et al. | |
| 2009/0209990 A1 | 8/2009 | Yates et al. | |
| 2009/0254094 A1 | 10/2009 | Knapp et al. | |
| 2010/0225073 A1 | 9/2010 | Porter et al. | |
| 2011/0077673 A1 | 3/2011 | Grubac et al. | |
| 2011/0121049 A1 | 5/2011 | Malinouskas et al. | |
| 2011/0125138 A1 | 5/2011 | Malinouskas et al. | |
| 2011/0139851 A1 | 6/2011 | McCuen | |
| 2011/0155783 A1 | 6/2011 | Rajappa et al. | |
| 2011/0174099 A1 | 7/2011 | Ross et al. | |
| 2011/0204119 A1 | 8/2011 | McCuen | |
| 2011/0218522 A1 | 9/2011 | Whitman | |
| 2011/0253765 A1 | 10/2011 | Nicholas et al. | |
| 2011/0290854 A1 | 12/2011 | Timm et al. | |
| 2011/0295242 A1 | 12/2011 | Spivey et al. | |
| 2011/0295269 A1 | 12/2011 | Swensgard et al. | |
| 2012/0000962 A1 | 1/2012 | Racenet et al. | |
| 2012/0089131 A1 | 4/2012 | Zemlok et al. | |
| 2012/0143002 A1 | 6/2012 | Aranyi et al. | |
| 2012/0223121 A1 | 9/2012 | Viola et al. | |
| 2012/0253329 A1 | 10/2012 | Zemlok et al. | |
| 2012/0310220 A1 | 12/2012 | Malkowski et al. | |
| 2012/0323226 A1 | 12/2012 | Chowaniec et al. | |
| 2013/0018361 A1 | 1/2013 | Bryant | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |

FOREIGN PATENT DOCUMENTS

| | | | |
|---|---|---|---|
| DE | 102008053842 A1 | 5/2010 | |
| EP | 0634144 | 1/1995 | |
| EP | 0648476 A1 | 4/1995 | |
| EP | 0686374 A2 | 12/1995 | |
| EP | 1690502 | 8/2006 | |
| EP | 1736112 | 12/2006 | |
| EP | 1769754 | 4/2007 | |
| EP | 1813199 A1 | 8/2007 | |
| EP | 1813203 | 8/2007 | |
| EP | 1813211 A2 | 8/2007 | |
| EP | 1943958 | 7/2008 | |
| EP | 1943976 | 7/2008 | |
| EP | 2005898 A2 | 12/2008 | |
| EP | 2027819 | 2/2009 | |
| EP | 2055243 | 5/2009 | |
| EP | 2098170 | 9/2009 | |
| EP | 2100561 | 9/2009 | |
| EP | 2165664 A2 | 3/2010 | |
| EP | 2236098 A2 | 10/2010 | |
| EP | 2263568 A2 | 12/2010 | |
| EP | 2329773 A1 | 6/2011 | |
| EP | 2333509 A1 | 6/2011 | |
| EP | 2462880 A2 | 6/2012 | |
| EP | 2491872 A1 | 8/2012 | |
| EP | 2586382 A2 | 5/2013 | |
| EP | 2606834 A2 | 6/2013 | |
| EP | 2676615 A2 | 12/2013 | |
| WO | WO 00/72760 | 12/2000 | |
| WO | WO 00/72765 | 12/2000 | |
| WO | 2003/000138 A2 | 1/2003 | |
| WO | WO 03/026511 | 4/2003 | |
| WO | WO 03/077769 | 9/2003 | |
| WO | WO 2004/107989 | 12/2004 | |
| WO | WO 2006/042210 | 4/2006 | |
| WO | WO 2007/014355 | 2/2007 | |
| WO | WO 2007/026354 | 3/2007 | |
| WO | WO 2008/131362 | 10/2008 | |
| WO | WO 2008/133956 | 11/2008 | |
| WO | WO 2009/039506 | 3/2009 | |
| WO | WO 2009/132359 | 10/2009 | |
| WO | 2011/108840 A2 | 9/2011 | |

OTHER PUBLICATIONS

Extended European Search Report corresponding to EP No. 13 16 3033.7, completed Jun. 27, 2013 and mailed Jul. 15, 2013; (8 pp).

Extended European Search Report corresponding to EP No. 12 18 6177.7, completed Aug. 14, 2013 and mailed Aug. 23, 2013; (8 pp).

Partial European Search Report corresponding to EP No. 13 17 1742.3, completed Sep. 17, 2013 and mailed Sep. 25, 2013; (8 pp).

Partial European Search Report corresponding to EP No. 13 17 2400.7, completed Sep. 18, 2013 and mailed Oct. 1, 2013; (7 pp).

Extended European Search Report corresponding to EP No. 13 17 5475.6, completed Sep. 23, 2013 and mailed Oct. 1, 2013; (8 pp).

Extended European Search Report corresponding to EP No. 13 17 5478.0, completed Sep. 24, 2013 and mailed Oct. 2, 2013; (6 pp).

Extended European Search Report corresponding to EP No. 13 17 5479.8, completed Sep. 27, 2013 and mailed Oct. 10, 2013; (7 pp).

(56) References Cited

OTHER PUBLICATIONS

Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
International Search Report corresponding to PCT/US2005/027266, completed May 30, 2008 and mailed Jun. 18, 2008; (2 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.

* cited by examiner

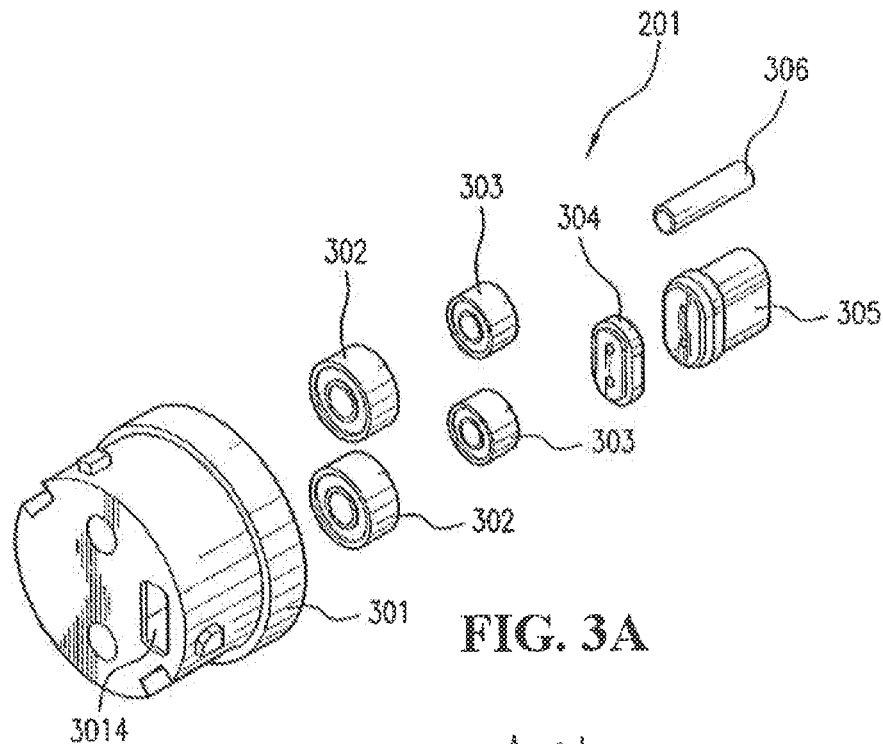
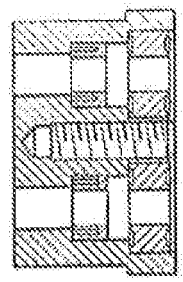
FIG. 3B
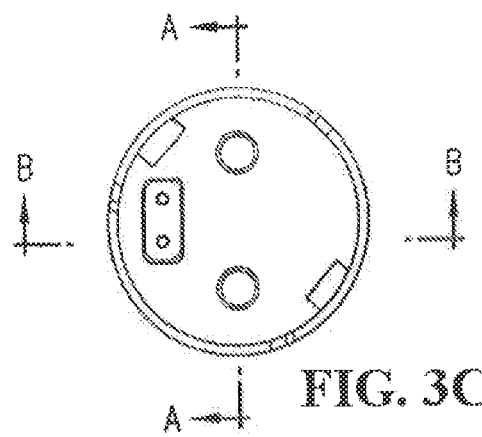
FIG. 3C
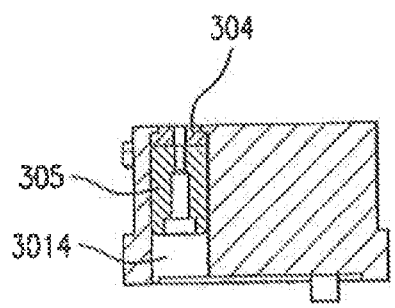
FIG. 3D
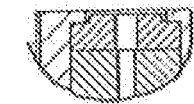
FIG. 3E

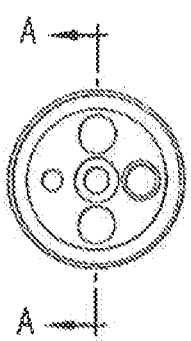
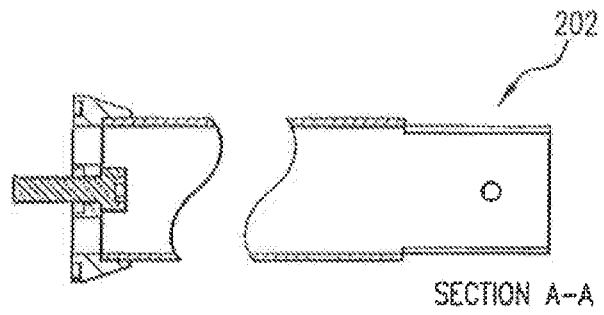
FIG. 7A  FIG. 7B
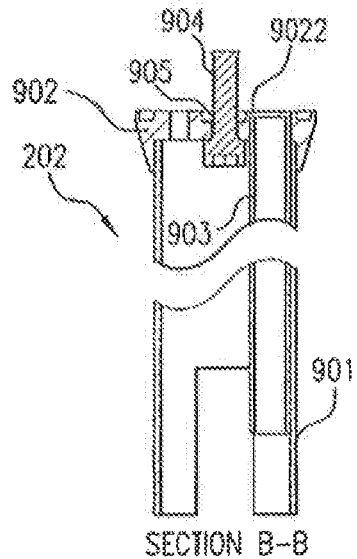
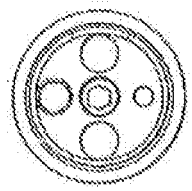
FIG. 7D  FIG. 7C
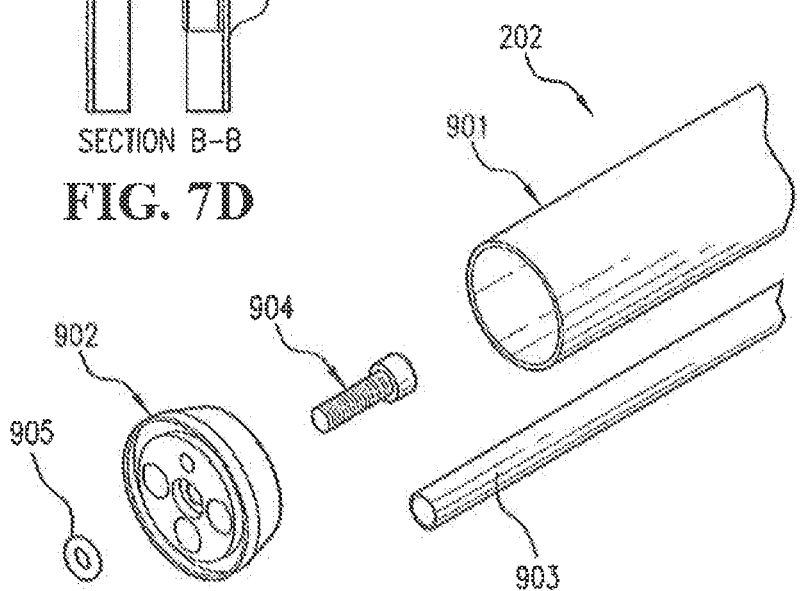
FIG. 7E

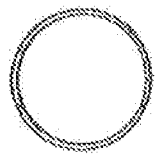
FIG. 8B
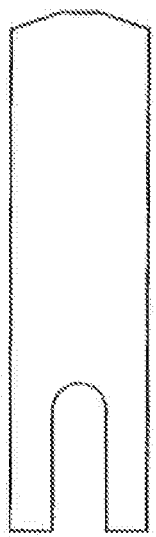
FIG. 8C
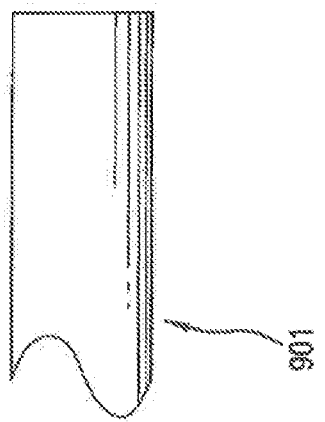
FIG. 8A
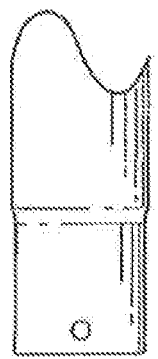

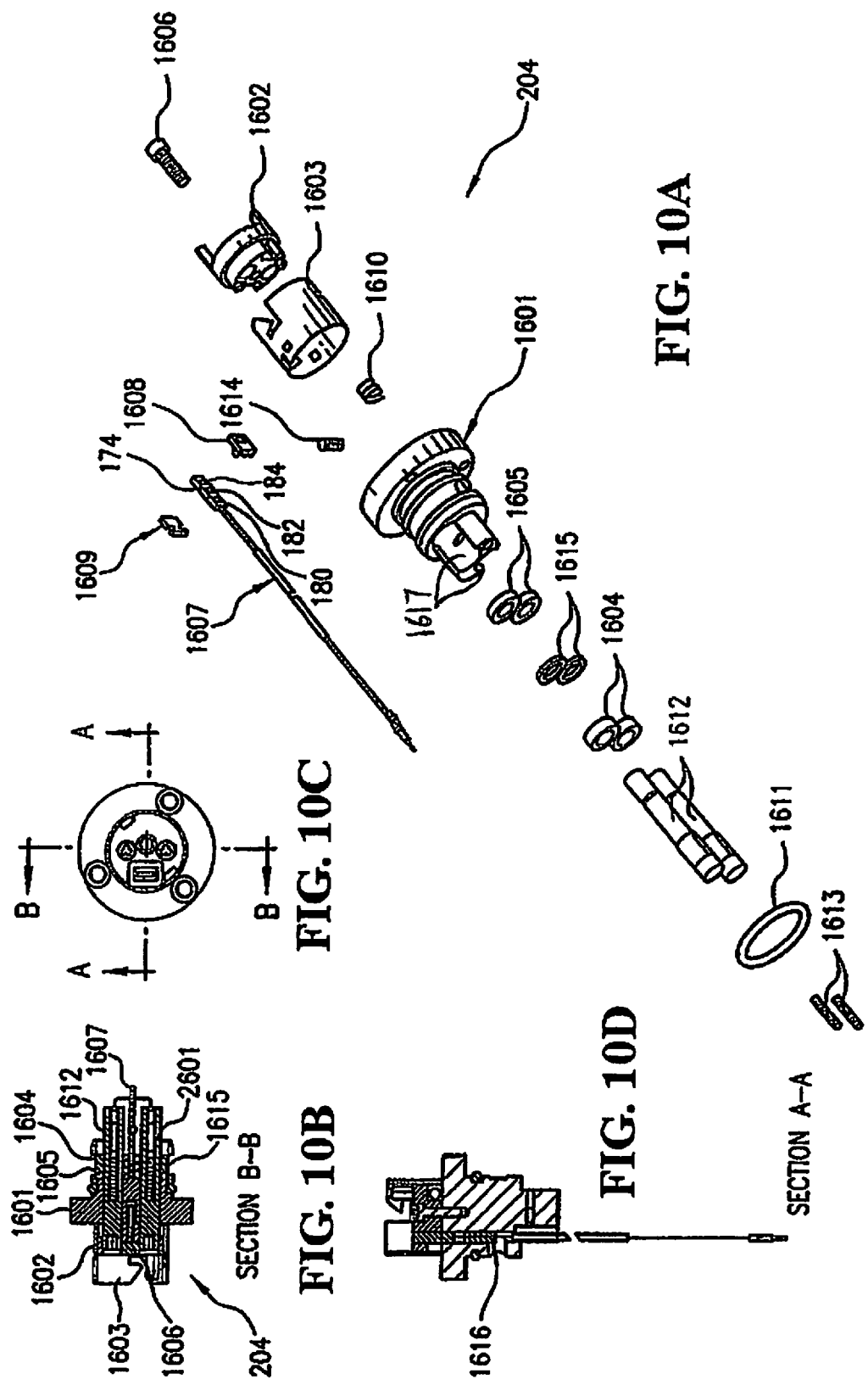

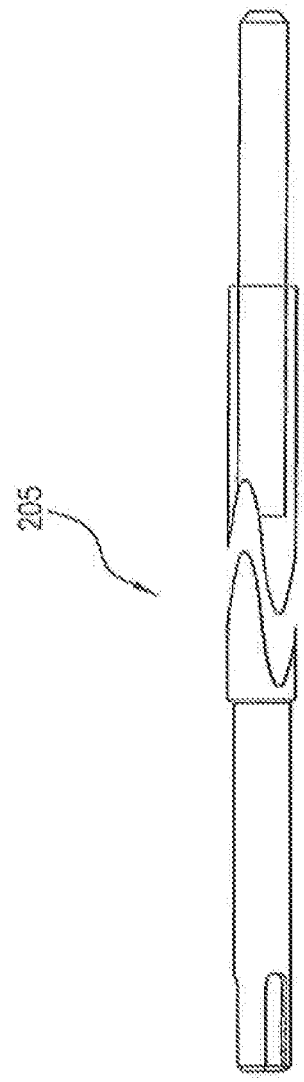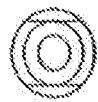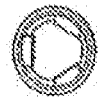
FIG. 17A
FIG. 17B
FIG. 17C

FLEXIBLE SHAFT EXTENDER AND METHOD OF USING SAME

CROSS-REFERENCE TO RELATED APPLICATIONS

This application is a Continuation of and claims the benefit of and priority to U.S. patent application Ser. No. 13/083,722, filed on Apr. 11, 2011, which is a Continuation of and claims the benefit of and priority to U.S. patent application Ser. No. 11/194,950, filed on Aug. 1, 2005 (now U.S. Pat. No. 7,947, 034), which claims the benefit of and priority to U.S. Provisional Patent Application Ser. No. 60/592,778, entitled "Flexible Shaft Extender," filed on Jul. 30, 2004, each of which is expressly incorporated herein in its entirety by reference.

FIELD OF THE INVENTION

The present invention relates to a surgical device, and more particularly to a flexible shaft extender, and a method for using same.

BACKGROUND

Various surgical systems are known in which a surgical attachment is attached to a flexible shaft. In these systems, a surgical attachment may typically be manipulated and/or positioned within the patient's body by the user holding the flexible shaft at a location near to the surgical attachment. For surgical locations within the patient's body that are difficult to access, the user may be required to hold the flexible shaft at a substantial distance from its point of connection to the surgical attachment. However, the flexibility of the flexible shaft may hinder a user's ability to accurately position the surgical attachment within the body. This may be problematic when the position of the surgical attachment is well within the patient's body and the user is forced to hold the flexible shaft at a substantial distance from its point of connection to the surgical attachment. The resulting lack of accuracy in positioning and manipulating the surgical attachment may negatively impact the effectiveness of the surgical attachment in performing the surgical procedure.

SUMMARY

The present invention relates to an extender for a flexible shaft of an electro-mechanical surgical system. The flexible shaft extender is substantially rigid. The flexible shaft extender is configured to be coupled at one end to the flexible shaft of an electro-mechanical surgical system and to be coupled at its other end to a surgical attachment. Advantageously, the flexible shaft extender includes a pair of rotatable drive shafts that are configured to engage and be secured with rotatable drive shafts of the flexible shaft of the electro-mechanical surgical system. In this manner, rotation of the rotatable drive shafts of the flexible shaft by an electro-mechanical driver device may cause the drive shafts of the flexible shaft extender to rotate, thereby rotating the complementary connectors of the surgical attachment so as to operate the surgical attachment.

Furthermore, the flexible shaft extender may include a data wiring harness or data cable which is configured to attach to and communicate with the surgical attachment and the data cable of the flexible shaft. In this manner, data, such as usage data, operating data, etc. may be conveyed via the flexible shaft extender between the surgical attachment and the data cable of the flexible shaft.

The present invention provides, in an example embodiment, for a surgical attachment used in an electro-mechanical surgical system that is coupleable to an electro-mechanical driver device via a flexible shaft, a substantially rigid extender that includes: a proximal end configured to be detachably coupled to a distal end of the flexible shaft; a distal end configured to be detachably coupled to the surgical attachment; at least one rotatable drive shaft configured to engage and be secured with a respective rotatable drive shaft of the flexible shaft such that rotation of the respective rotatable drive shaft of the flexible shaft by the electro-mechanical driver device causes the at least one rotatable drive shaft of the extender to rotate, thereby rotating a complementary connector of the surgical attachment so as to operate the surgical attachment. The extender may be autoclavable. The extender may include a memory unit. The memory unit may be configured to store one or more of serial number data, an attachment type identifier data and a usage data. One or more of the serial number data and the ID data may be configured as read-only data. The serial number data may be data uniquely identifying the extender. The ID data may be data identifying the type of the extender. The usage data may represent a number of times the extender has been used. The extender may include a data cable configured to transfer data between the memory unit and the electro-mechanical driver device. The extender may also include a data cable configured to transfer data-between a memory unit located in the surgical attachment and the electro-mechanical driver device.

The present invention also provides, in an example embodiment, a method for performing a surgical procedure, the method comprising the steps of: detachably coupling a proximal end of an extender to a flexible shaft, the flexible shaft being coupled to an electro-mechanical driver device, the extender being substantially rigid; detachably coupling a distal end of the extender to a surgical attachment such that at least one rotatable drive shaft engages and is secured with a respective rotatable drive shaft of the flexible shaft; rotating the respective rotatable drive shaft of the flexible shaft by the electro-mechanical driver device so as to cause the at least one rotatable drive shaft of the extender to rotate; and rotating, by the at least one rotatable drive shaft of the extender, a complementary connector of the surgical attachment so as to operate the surgical attachment. The method may include the step of storing in a memory unit of the extender one or more of serial number data, an attachment type identifier data and a usage data. The method may include the step of configuring one or more of the serial number data and the ID data as read-only data. The serial number data may be data uniquely identifying the extender. The ID data may be data identifying the type of the extender. The usage data may represent a number of times the extender has been used. The method may include the step of transferring, via a data cable located within the extender, data between the memory unit and the electro-mechanical driver device. The method may include the step of storing in a memory unit of the surgical attachment one or more of serial number data, an attachment type identifier data and a usage data. The method may also include the step of transferring, via a data cable located within the extender, data between the memory unit and the electro-mechanical driver device.

Additional features of the flexible shaft extender of the present invention are discussed in greater detail below.

BRIEF DESCRIPTION OF THE DRAWINGS

FIGS. 3A to 3E illustrate various views of the distal tip assembly, according to an example embodiment of the present invention.

FIGS. 7A to 7E illustrate various views of the tube assembly, according to an example embodiment of the present invention.

FIGS. 8A to 8C illustrate various views of the tube, according to an example embodiment of the present invention.

FIGS. 10A to 10D illustrate various views of the handle cap assembly, according to an example embodiment of the present invention.

FIGS. 17A to 17C illustrate various views of the drive shafts, according to an example embodiment of the present invention.

DETAILED DESCRIPTION

Figure 1A:
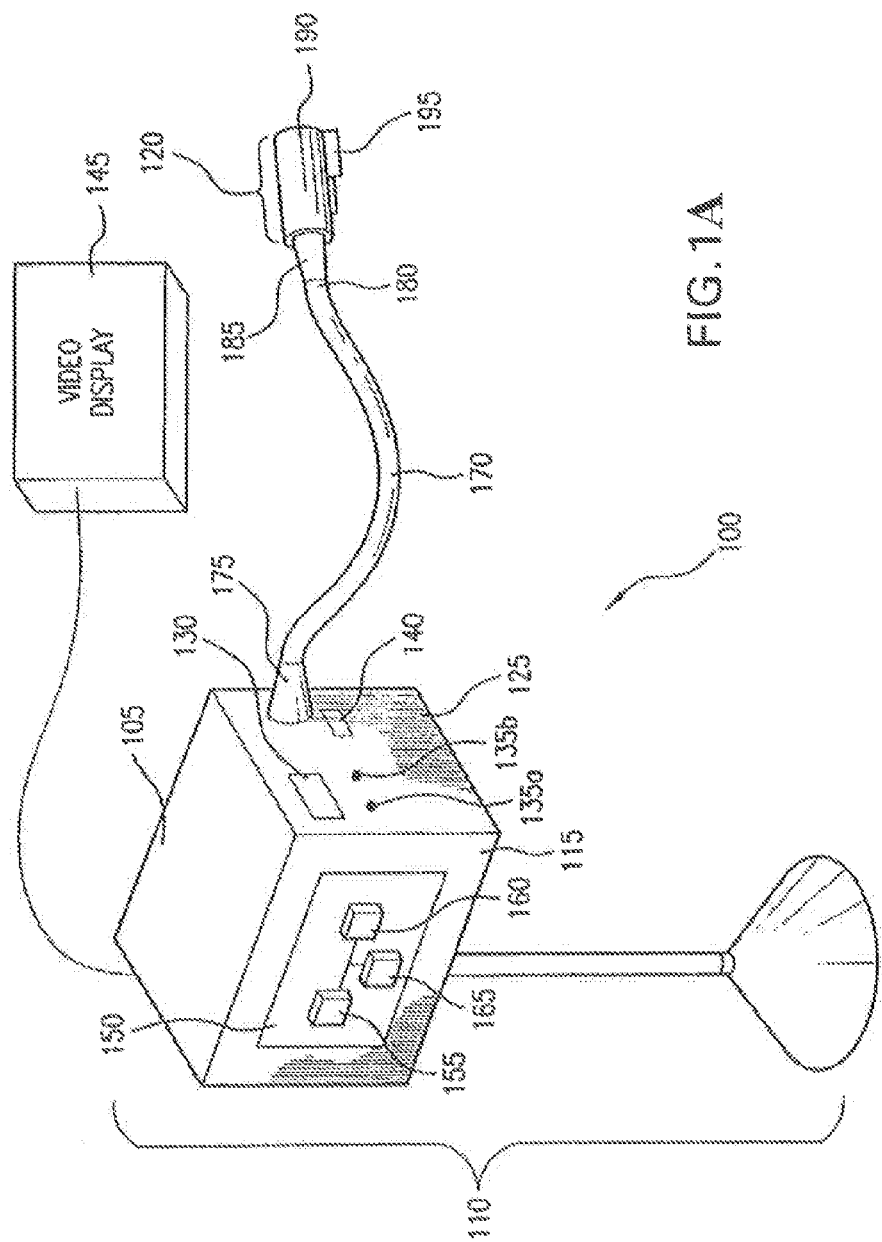
FIG. 1A is a surgical system, according to an example embodiment of the present invention.

FIG. 1A is a surgical system 100, according to an example embodiment of the present invention. The surgical system 100 includes an electro-mechanical driver device 110 detachably coupled to a surgical attachment 120. Such an electromechanical driver device is described in, for example, U.S. patent application Ser. No. 09/723,715, entitled "Electro-Mechanical Surgical Device," filed on Nov. 28, 2000, now issued as U.S. Pat. No. 6,793,652, U.S. patent application Ser. No. 09/836,781, entitled "Electro-Mechanical Surgical Device, filed on Apr. 17, 2001, now issued as U.S. Pat. No. 6,981,941, and U.S. patent application Ser. No. 09/887,789, entitled "Electro-Mechanical Surgical Device," filed on Jun. 22, 2001, now issued as U.S. Pat. No. 7,032,798, each of which is expressly incorporated herein in its entirety by reference. The electro-mechanical driver device 110 may include, for example, a remote power console (RPC) 105, which includes a housing 115 having a front panel 125. Mounted on the front panel 125 are a display device 130 and indicators 135a, 135b. A connection slot 140 is also provided on the front panel 125. The electro-mechanical driver device 110 may also include a video display 145, e.g., a television monitor, computer monitor, CRT or other viewing device, attached to the RPC 105. The video display 145 may receive, for example, image signals (e.g., video signals) from an imaging device 195. The electro-mechanical driver device 110 may also include a reception system 150 having a receiver or transceiver 155 and circuitry 160 operable to convert signals received from the imaging device 195 into a form suitable for display on the video display 145. The reception system 150 may also include a memory device 165 for buffering and/or storing processed image data received from the imaging device 195.

A flexible shaft 170 may extend from the housing 115 and may be detachably secured thereto via a first coupling 175. The distal end 180 of the flexible shaft 170 may include a second coupling 185 adapted to detachably secure the surgical attachment 120 to the distal end 180 of the flexible shaft 170.

Disposed within the interior channel of the flexible shaft 170, and extending along the length thereof, may be rotatable shafts, steering cables, one or more data transfer cables and power transfer leads, all of which terminate at the second coupling 185 at the distal end 180 of the flexible shaft 170. The electro-mechanical driver device 110 may include a motor system (not shown), which includes one or more motors configured to rotate the drive shafts and to apply tension or otherwise drive the steering cables to thereby steer the distal end 180 of the flexible shaft 170.

Various types of surgical instruments or attachments 190 may be attached to the distal end 180 of the flexible shaft 170. The surgical instrument or attachment may be, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. patent application Ser. No. 09/324,451, entitled "A Stapling Device for Use with an Electromechanical Driver Device for Use with Anastomosing, Stapling, and Resecting Instruments," now issued as U.S. Pat. No. 6,315, 184, U.S. patent application Ser. No. 09/324,452, entitled "Electro-mechanical Driver Device for Use with Anastomosing, Stapling, and Resecting Instruments," now issued as U.S. Pat. No. 6,443,973, U.S. patent application Ser. No. 09/351, 534, entitled "Automated Surgical Stapling System," now issued as U.S. Pat. No. 6,264,087, U.S. patent application Ser. No. 09/510,926, entitled "A Vessel and Lumen Expander Attachment for Use with an Electro-mechanical Driver Device," now issued as U.S. Pat. No. 6,378,061, U.S. patent application Ser. No. 09/510,927, entitled "Electro-mechanical Driver and Remote Surgical Instruments Attachment Having Computer Assisted Control Capabilities," now issued as U.S. Pat. No. 6,716,233, U.S. patent application Ser. No. 09/510,931, entitled "A Tissue Stapling Attachment for Use with an Electro-mechanical Driver Device," now issued as U.S. Pat. No. 6,533,157, U.S. patent application Ser. No. 09/510,932, entitled "A Fluid Delivery Mechanism for Use with Anastomosing, Stapling, and Resecting Instruments," now issued as U.S. Pat. No. 6,491,201, and U.S. patent application Ser. No. 09/510,933, entitled "A Fluid Delivery Device for Use with Anastomosing, Stapling, and Resecting Instruments," now issued as U.S. Pat. No. 6,488,197, each of which is expressly incorporated herein in its entirety by reference thereto.

Figure 1B:
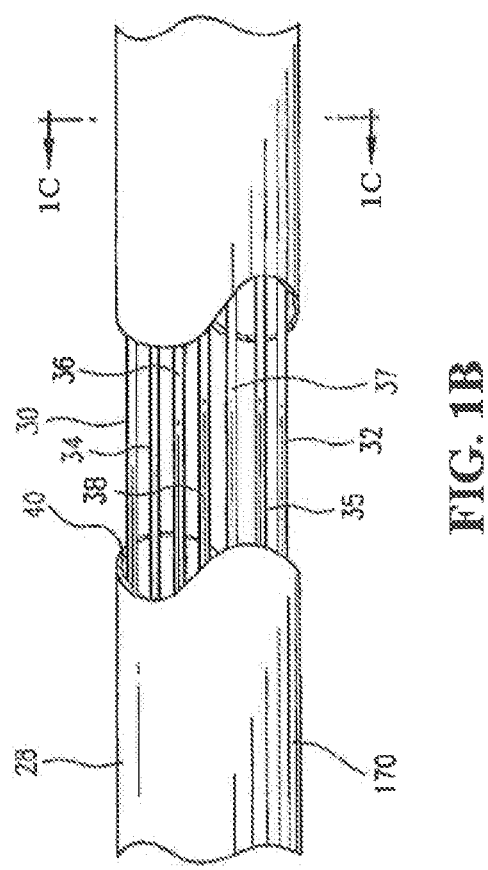
FIG. 1B is a side view, partially in section, of a flexible shaft, according to an example embodiment of the present invention.
Figure 1C:
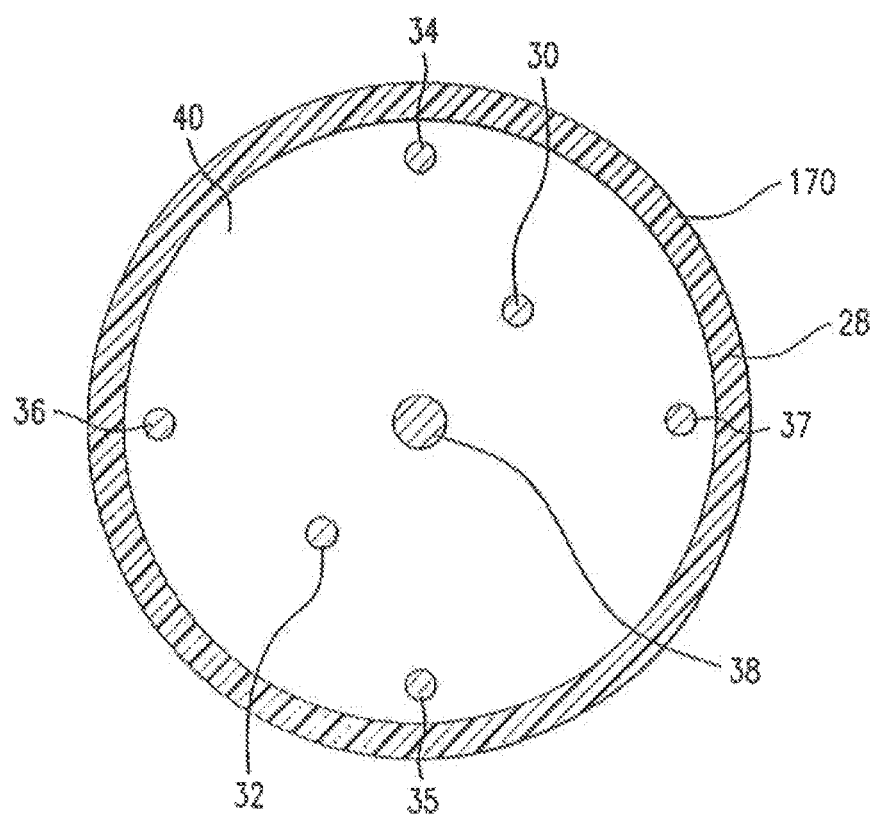
FIG. 1C is a cross-sectional view of the flexible shaft taken along the line 1C-1C shown in FIG. 1B.

Referring to FIG. 1B, there is seen a side view, partially in section, of the flexible shaft 170. According to an example embodiment, the flexible shaft 170 includes a tubular sheath 28, which may include a coating or other sealing arrangement to provide a fluid-tight seal between the interior channel 40 thereof and the environment. The sheath 28 may be formed of a tissue-compatible, sterilizable elastomeric material. The sheath 28 may also be formed of a material that is autoclavable. Disposed within the interior channel 40 of the flexible shaft 170, and extending along the entire length thereof, may be a first rotatable drive shaft 30, a second rotatable drive shaft 32, a first steering cable 34, a second steering cable 35, a third steering cable 36, a fourth steering cable 37 and a data transfer cable 38. FIG. 1C is a cross-sectional view of the flexible shaft 170 taken along the line 1C-1C shown in FIG. 1B and further illustrates the several cables 30, 32, 34, 35, 36, 37, 38. Each distal end of the steering cables 34, 35, 36, 37 is affixed to the distal end 180 of the flexible shaft 170. Each of the several cables 30, 32, 34, 35, 36, 37, 38 may be contained within a respective sheath.

Figure 1D:
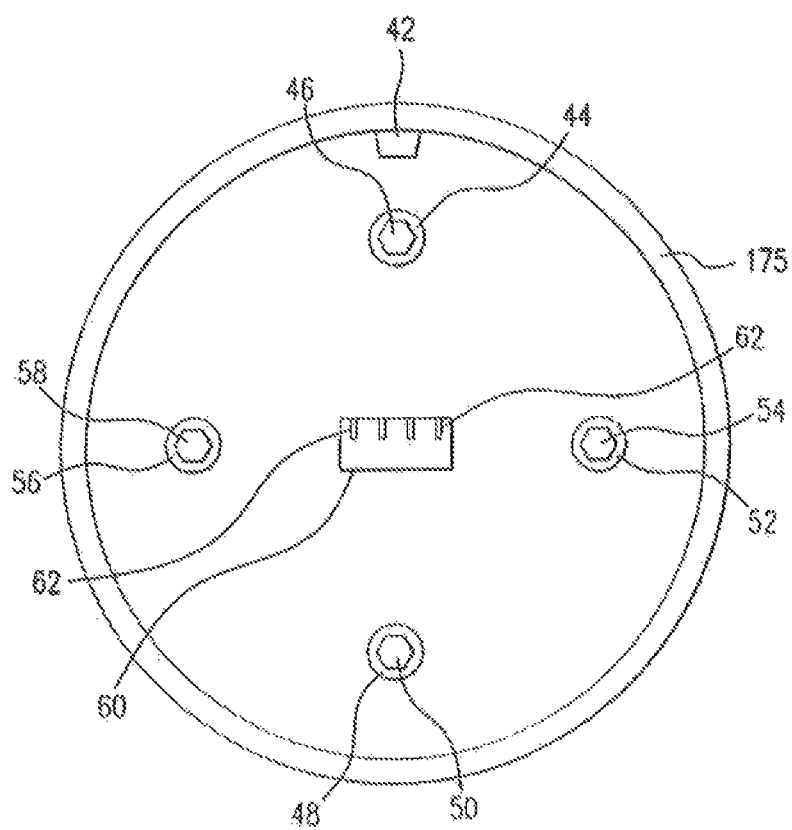
FIG. 1D is a rear end view of a first coupling of the flexible shaft, according to an example embodiment of the present invention.

Referring now to FIG. 1D, there is seen a rear end view of the first coupling 175. The first coupling 175 includes a first connector 44, a second connector 48, a third connector 52 and a fourth connector 56, each rotatably secured to the first coupling 175. Each of the connectors 44, 48, 52, 56 includes a respective recess 46, 50, 54, 58. As shown in FIG. 1D, each recess 46, 50, 54, 58 may be hexagonally shaped. It should be appreciated, however, that the recesses 46, 50, 54, 58 may have any shape and configuration to non-rotatably couple and rigidly attach the connectors 44, 48, 52, 56 to respective drive shafts of the motor arrangement contained within the housing 12, as more fully described below. It should be appreciated that complementary projections may be provided on respective drive shafts of the motor arrangement to thereby drive the drive elements of the flexible shaft 170 as described below. It should also be appreciated that the recesses may be provided on the drive shafts and complementary projections may be provided on the connectors 44, 48, 52, 56. Any other coupling arrangement configured to non-rotatably and releasably couple the connectors 44, 48, 52, 56 and the drive shafts of the motor arrangement may be provided.

One of the connectors 44, 48, 52, 56 is non-rotatably secured to the first drive shaft 30, and another one of the connectors 44, 48, 52, 56 is non-rotatably secured to the second drive shaft 32. The remaining two of the connectors 44, 48, 52, 56 engage with transmission elements configured to apply tensile forces on the steering cables 34, 35, 36, 37 to thereby steer the distal end 180 of the flexible shaft 170. The data transfer cable 38 is electrically and logically connected with the data connector 60. The data connector 60 includes, for example, electrical contacts 62, corresponding to and equal in number to the number of individual wires contained in the data cable 38. The first coupling 175 includes a key structure 42 to properly orient the first coupling 175 to a mating and complementary coupling arrangement disposed on the housing 115. Such key structure 42 may be provided on either one, or both, of the first coupling 175 and the mating and complementary coupling arrangement disposed on the housing 115. The first coupling 175 may include a quick-connect type connector, which may use, for example, a simple pushing motion to engage the first coupling 175 to the housing 115. Seals may be provided in conjunction with any of the several connectors 44, 48, 52, 56, 60 to provide a fluid-tight seal between the interior of the first coupling 175 and the environment.

Figure 1E:
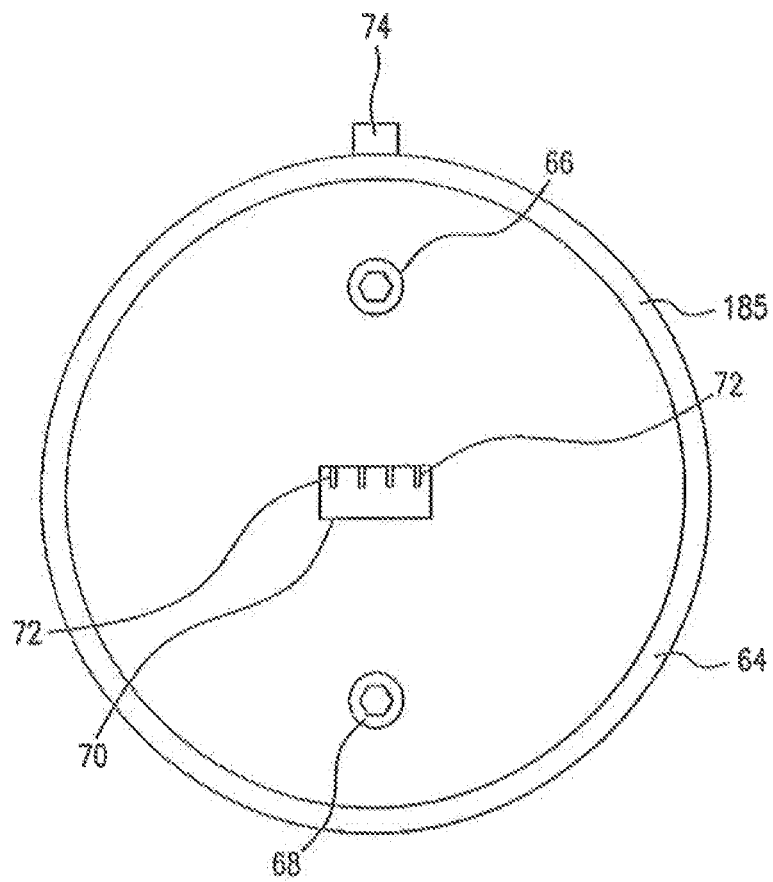
FIG. 1E is a front end view of a second coupling of the flexible shaft, according to an example embodiment of the present invention.

Referring now to FIG. 1E, there is seen a front end view of the second coupling 185 of the flexible shaft 170. The second coupling 185 includes a first connector 66 and a second connector 68, each being rotatably secured to the second coupling 185 and each being non-rotatably secured to a distal end of a respective one of the first and second drive shafts 30, 32. A quick-connect type fitting 64 is provided on the second coupling 185 for detachably securing the surgical instrument or attachment thereto. The quick-connect type fitting 64 may be, for example, a rotary quick-connect type fitting, a bayonet type fitting, etc. A key structure 74 is provided on the second coupling 185 for properly aligning the surgical instrument or attachment to the second coupling 185. The key structure or other arrangement for properly aligning the surgical instrument or attachment to the flexible shaft 170 may be provided on either one, or both, of the second coupling 185 and the surgical instrument or attachment. In addition, the quick-connect type fitting may be provided on the surgical instrument or attachment. A data connector 70, having electrical contacts 72, is also provided in the second coupling 185. Like the data connector 60 of the first coupling 175, the data connector 70 of the second coupling 185 includes the contacts 72 electrically and logically connected to the respective wires of the data transfer cable 38 and the contacts 62 of the data connector 60. Seals may be provided in conjunction with the connectors 66, 68, 70 to provide a fluid-tight seal between the interior of the second coupling 185 and the environment.

Disposed within the housing 115 of the remote power console 105 are electro-mechanical driver elements configured to drive the drive shafts 30, 32 and the steering cables 34, 35, 36, 37 to thereby operate the electro-mechanical surgical device 10 and the surgical instrument or attachment attached to the second coupling 185. Electric motors, each operating via a power source, may be disposed in the remote power console 105. Any appropriate number of motors may be provided, and the motors may operate via battery power, line current, a DC power supply, an electronically controlled DC power supply, etc. It should also be appreciated that the motors may be connected to a DC power supply, which is in turn connected to line current and which supplies the operating current to the motors.

Figure 2:
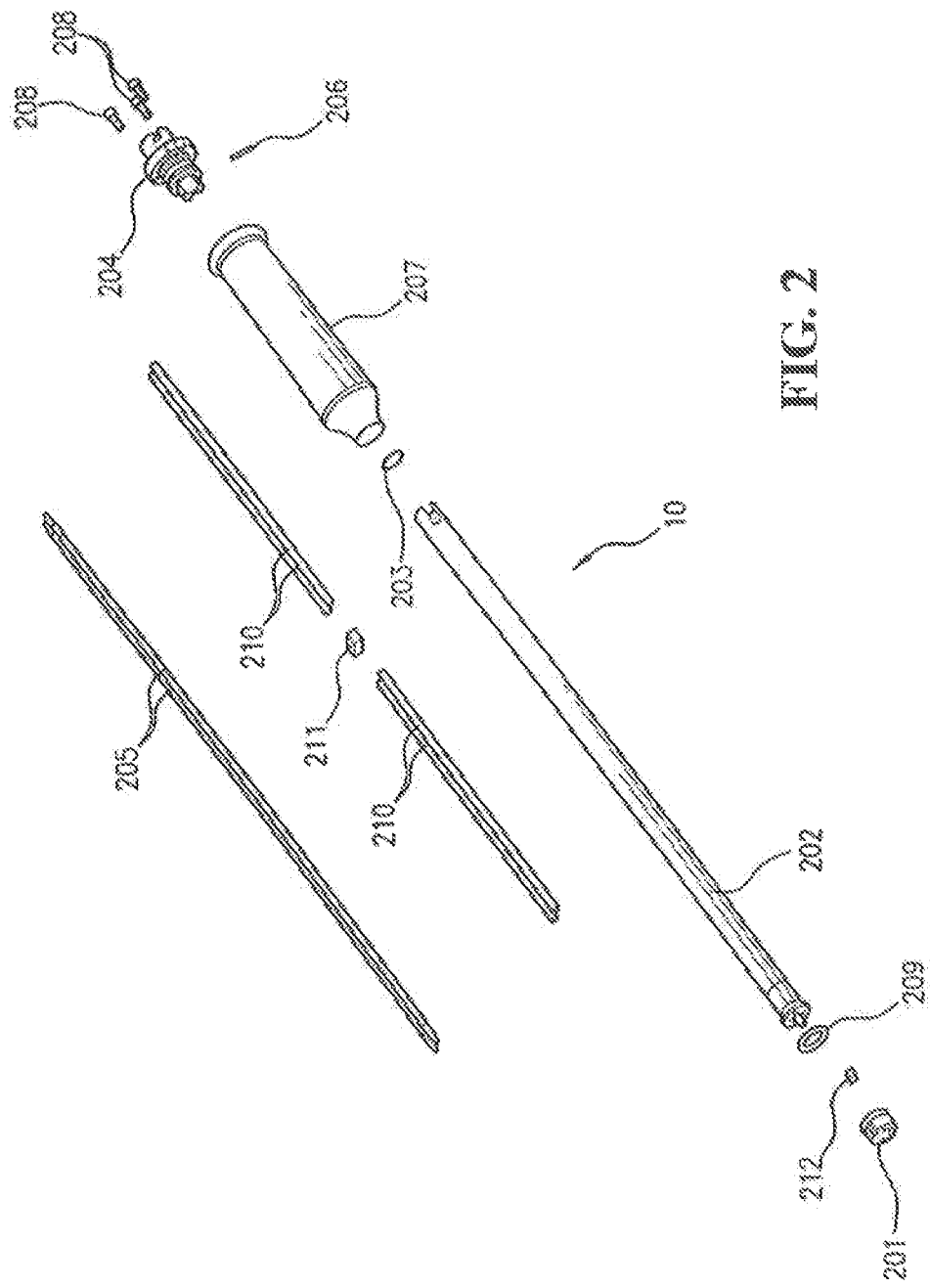
FIG. 2 is an exploded perspective view of a flexible shaft extender, according to an example embodiment of the present invention.
Figure 4B:
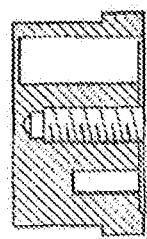
FIGS. 4A to 4D illustrate various views of the distal end tip, according to an example embodiment of the present invention.
Figure 4D:
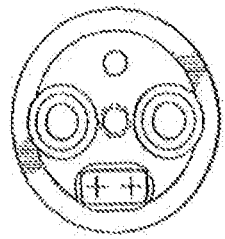
Figure 4A:
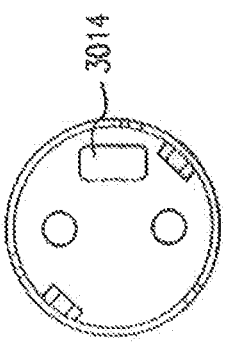
Figure 4C:
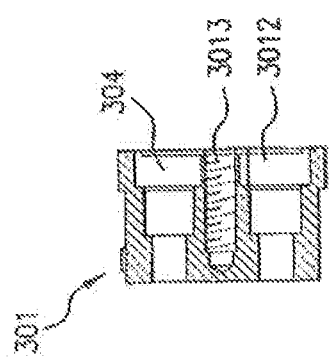
Figure 5E:
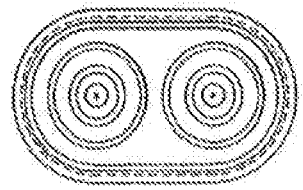
FIGS. 5A to 5E illustrate various views of the DLU pin sealing element, according to an example embodiment of the present invention.
Figure 5B:
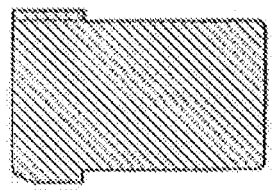
Figure 5D:
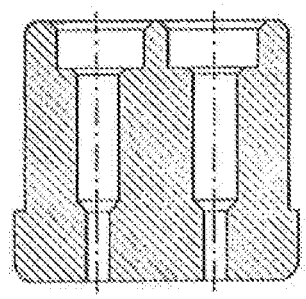
Figure 5A:
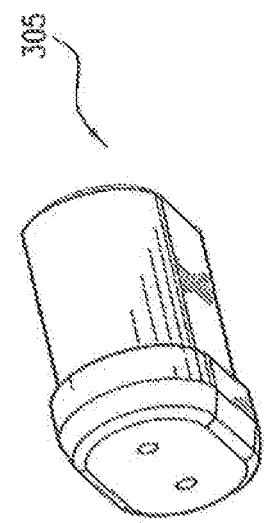
Figure 5C:
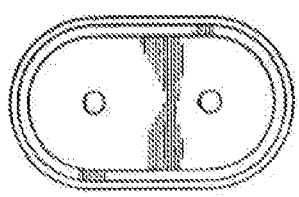

FIG. 2 is an exploded perspective view of a flexible shaft extender 10, according to an example embodiment of the present invention. The flexible shaft extender 10 provides a substantially rigid handle that attaches to the second coupling 185 at the distal end 180 of the flexible shaft 170. The flexible shaft extender 10 includes a distal tip assembly 201, a tube assembly 202, a distal end O-ring 203, a handle cap assembly 204, a pair of drive shafts 205, a retention pin 206, a handle 207, a handle screw 208, a handle O-ring 209, a pair of tubes (e.g., of teflon) 210, a bearing block 211 and a pin block 212.

FIGS. 3A to 3E illustrate various views of the distal tip assembly 201. As shown in FIG. 3A, the distal tip assembly 201 includes a distal end tip 301, a pair of bearings 302, a pair of sealing elements 303, a distal pin positioner 304, a DLU pin sealing element 305 and a dowel pin 306. The distal tip assembly 201 is configured to have a surgical attachment attached thereto. When the flexible shaft extender 10 is assembled, the distal tip assembly 201 is attached to the distal end of the tube assembly 202.

FIGS. 4A to 4D illustrate various views of the distal end tip 301. The distal end tip 301 includes two stepped bores 3011 and 3012. In addition, the distal end tip 301 includes a centrally-located threaded bore 3013. In addition, the distal end tip 301 includes a rectangular longitudinal opening 3014.

Figure 6B:
FIGS. 6A to 6C illustrate various views of the distal pin positioner, according to an example embodiment of the present invention.
Figure 6C:
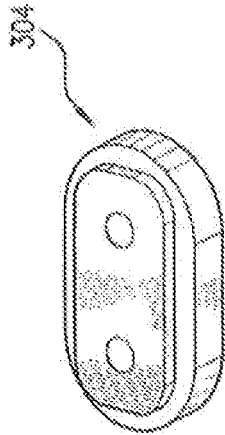
Figure 6A:
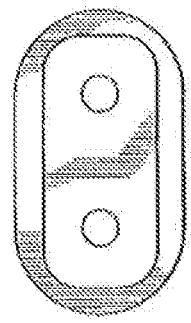

FIGS. 5A to 5E illustrate various views of the DLU pin sealing element 305. FIGS. 6A to 6C illustrate various views of the distal pin positioner 304.

Referring back to FIGS. 3B and 3D, there is shown the various components of the distal tip assembly 201 in the assembled condition. As shown in FIG. 3B, the pair of bearings 302 are inserted within the two stepped bores 3011 and 3012 of the distal end tip 301. As shown in FIGS. 3D and 3E, the distal pin positioner 304 is inserted into the distal end tip 301 and fits within the rectangular longitudinal opening 3014 and is flush with the distal-most surface of the distal end tip. The DLU pin sealing element 305 maintains the distal pin positioner 304 within the rectangular longitudinal opening 3014 of the distal end tip 301.

FIGS. 7A to 7E illustrate various views of the tube assembly 202. For instance, FIG. 7E is an exploded view of the tube assembly 202. The tube assembly 202 includes a tube 901, a tube cap 902, a wire retention tube 903, a screw 904 and a distal end O-ring 905.

Figure 9B:
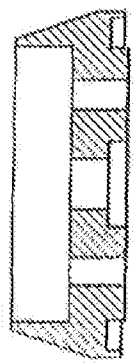
FIGS. 9A to 9C illustrate various views of the tube cap, according to an example embodiment of the present invention.
Figure 9C:
Figure 9A:
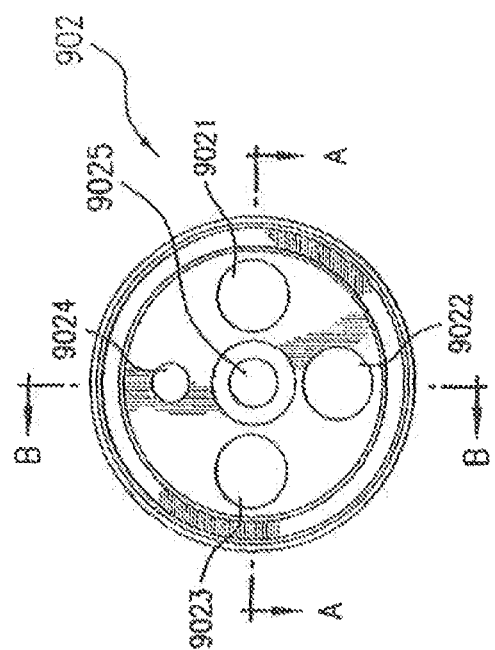
Figure 11C:
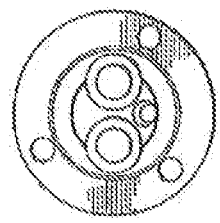
FIGS. 11A to 11E illustrate various views of the handle cap, according to an example embodiment of the present invention.
Figure 11E:
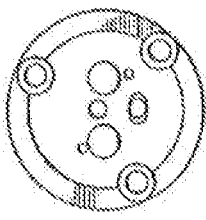
Figure 11B:
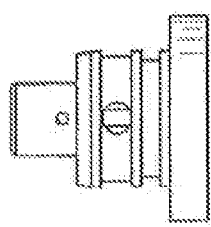
Figure 11D:
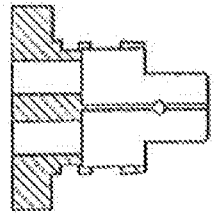
Figure 11A:
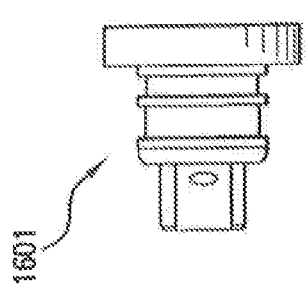
Figure 12D:
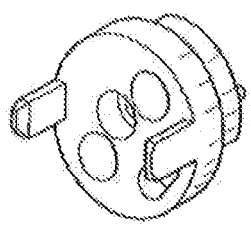
FIGS. 12A to 12J illustrate various views of the keyplate, according to an example embodiment of the present invention.
Figure 12H:
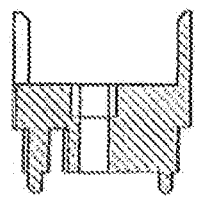
Figure 12C:
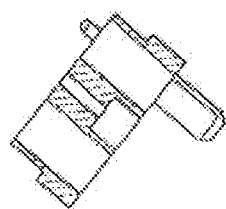
Figure 12G:
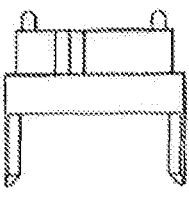
Figure 12B:
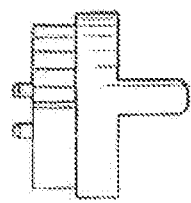
Figure 12F:
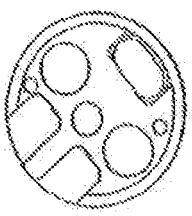
Figure 12J:
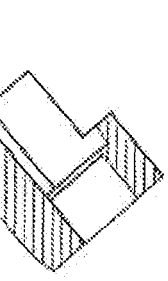
Figure 12A:
Figure 12E:
Figure 12I:
Figure 13D:
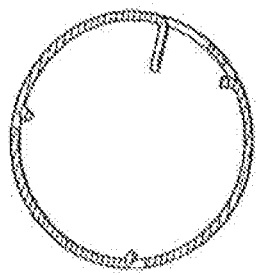
FIGS. 13A to 13G illustrate various views of the quick connect collar, according to an example embodiment of the present invention.
Figure 13G:
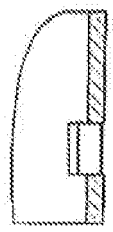
Figure 13C:
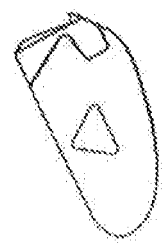
Figure 13F:
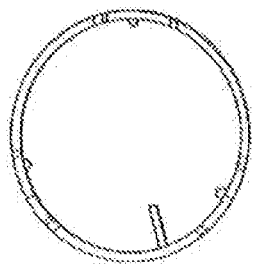
Figure 13B:
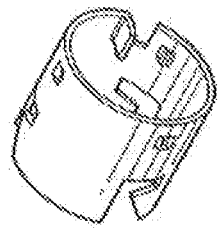
Figure 13A:
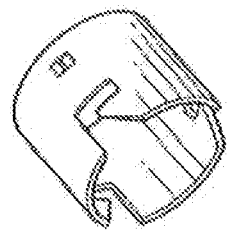
Figure 13E:
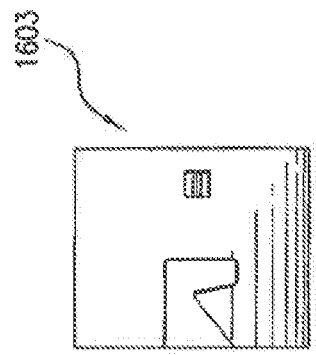

FIGS. 8A to 8C illustrate various views of the tube 901. FIGS. 9A to 9C illustrate various views of the tube cap 902. The tube cap 902 may include first second, third and fourth orifices 9021, 9022, 9023 and 9024 and a central orifice 9025.

Referring back to FIG. 7D, there is shown the various components of the tube assembly 202 in the assembled condition. As shown in FIG. 7D, the tube 901 may be welded to the tube cap 902. The wire retention tube 903 is arranged longitudinally within the tube 901 and may be welded to the tube cap 902 so as to be longitudinally aligned with the orifice 9022 of the tube cap 902. The screw 904 is inserted through the central orifice 9025 of the tube cap. The distal end O-ring 905 is retained around the screw 904 in a distal recess of the tube cap 902.

FIGS. 10A to 10D illustrate various views of the handle cap assembly 204. FIG. 10A is an exploded view of the handle cap assembly 204. The handle cap assembly 204 includes a handle cap 1601, a keyplate 1602, a quick connect collar 1603, a pair of bearings 1604, a pair of proximal sealing elements 1605, a screw 1606, a wiring harness assembly 1607, an outboard shim 1608, an inboard shim 1609, a spring 1610, a handle O-ring 1611, a drive socket assembly 1612, a drive socket spring 1613, a quick connect spring 1614, a bearing spacer 1615 and potting 1616.

The wiring harness assembly 1607 includes at its proximal end a device having a connector (e.g., for connection to the data transfer cable 38 of the flexible shaft 170), a memory unit 174 that may store various types of data, and one or more wires or cables extending distally therefrom. An exemplary memory unit 174 is described in, for example, U.S. patent application Ser. No. 09/723,715, entitled "Electro-Mechanical Surgical Device," filed on Nov. 28, 2000, now issued as U.S. Pat. No. 6,793,652, U.S. patent application Ser. No. 09/836,781, entitled "Electro-Mechanical Surgical Device, filed on Apr. 17, 2001, now issued as U.S. Pat. No. 6,981,941, and U.S. patent application Ser. No. 09/887,789, entitled "Electro-Mechanical Surgical Device," filed on Jun. 22, 2001, now issued as U.S. Pat. No. 7,032,798, each of which, as stated above, is expressly incorporated herein in its entirety by reference. For instance, the memory unit 174 may store, for instance, serial number data 180, an attachment type identifier data 182 and a usage data 184. Memory unit 174 may additionally store other data. Both the serial number data 180 and the ID data 182 may be configured as read-only data. In the example embodiment, serial number data 180 is data uniquely identifying the particular flexible shaft extender, whereas the ID data 182 is data identifying the type of the flexible shaft extender, such as, for example, a flexible shaft extender of a given length. The usage data 184 represents usage of the particular flexible shaft extender, such as, for example, the number of times the flexible shaft extender has been used.

It should be appreciated that the flexible shaft extender 10 may be designed and configured to be used a single time or multiple times. Accordingly, the usage data 184 may be used to determine whether the flexible shaft extender 10 has been used and whether the number of uses has exceeded the maximum number of permitted uses. An attempt to use the flexible shaft extender 10 after the maximum number of permitted uses has been reached may generate an ERROR condition.

FIGS. 11A to 11E illustrate various views of the handle cap 1601. FIGS. 12A to 12J illustrate various views of the keyplate 1602. FIGS. 13A to 13G illustrate various views of the quick connect collar 1603.

Figure 14:
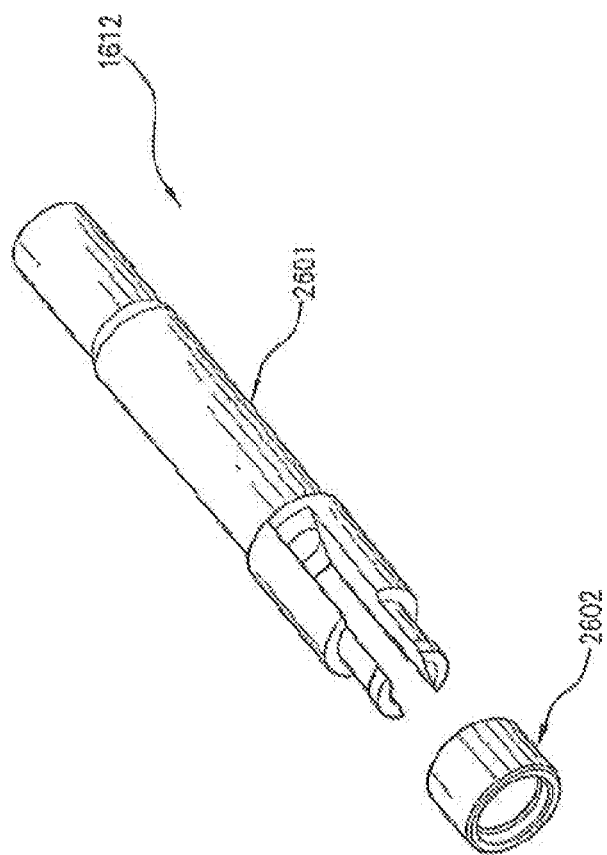
FIG. 14 is an exploded view of the drive socket assembly, according to an example embodiment of the present invention.
Figure 15C:
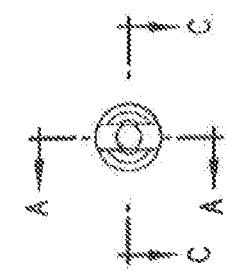
FIGS. 15A to 15F illustrate various views of the drive socket spring, according to an example embodiment of the present invention.
Figure 15F:
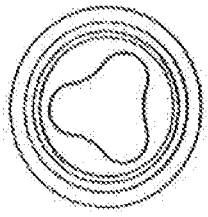
Figure 15B:
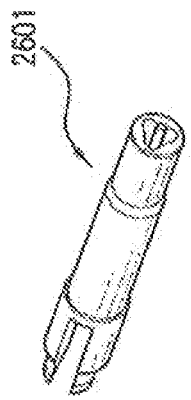
Figure 15E:
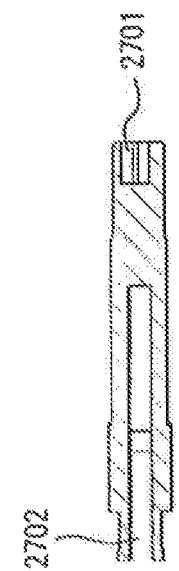
Figure 15A:
Figure 15D:
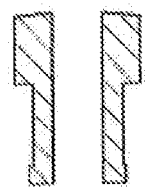
Figure 16A:
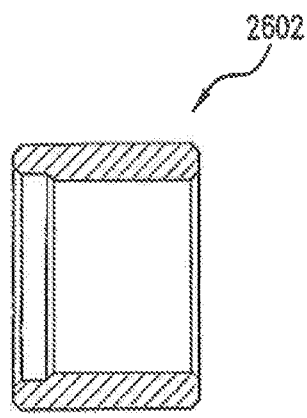
FIGS. 16A and 16B illustrate various views of the drive socket sleeve, according to an example embodiment of the present invention.
Figure 16B:
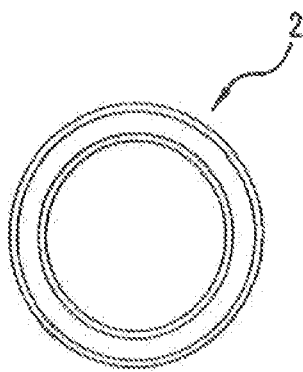

FIG. 14 is an exploded view of the drive socket assembly 1612. The drive socket assembly 1612 includes a drive socket 2601 and a drive socket sleeve 2602. FIGS. 15A to 15F illustrate various views of the drive socket spring 2601. The drive socket spring 2601 has a longitudinal slit 2702 at its distal end and a centrally-disposed, longitudinally-arranged bore 2701. FIGS. 16A and 16B illustrate various views of the drive socket sleeve 2602.

Referring back to FIG. 10B, there is shown the various components of the handle cap assembly 204 in the assembled condition. As shown in FIG. 10B, the keyplate 1602 is mounted to the proximal surface of the handle cap 1601 by the screw 1606. The quick connect collar 1603 is retained against the proximal surface of the handle cap 1601 by being in locked engagement between the keyplate 1602 and the handle cap 1601. The quick connect collar 1603 is configured to be detachably coupled to the second coupling 185 at the distal end 180 of the flexible shaft 170. The pair of bearings 1604 fit within corresponding orifices 1617 of the handle cap 1601. The pair of orifices 1617 of handle cap 1601 are configured to engage and rotatably secure to a corresponding one of the first rotatable drive shaft 30 and the second rotatable drive shaft 32 of the electro-mechanical driver device 110. In particular, one each of the bearing spacers 1615, the proximal sealing elements 1605 and the bearings 1604 are mounted on a respective drive socket 2601, and operate to rotatably retain the drive socket 2601 within respective orifices 1617 of the handle cap 1601 and, in turn, the drive sockets 2601 non-rotatably retain corresponding rotatable drive shafts 30, 32 of the electro-mechanical driver device 110. The wiring harness 1607 is retained within the handle cap assembly 204 such that a proximal end is accessible via an opening in the keyplate 1602, and a distal end extends to the distal end of the tube assembly 202 and out of an orifice of the distal tip assembly 201. In this manner, data may be conveyed via the wiring harness 1607 from a surgical attachment attached to the distal tip assembly 201 to the data transfer cable 38 within the flexible shaft 170.

FIGS. 17A to 17C illustrate various views of the drive shafts 205. In the example embodiments discussed and illustrated herein, the flexible shaft extender 10 includes two drive shafts 205, though any number, e.g., one or more, drive shafts may be employed. The drive shafts 205 are rotatable within the flexible shaft extender 10 so as to rotate a respective component of the surgical attachment. The proximal ends of the drive shafts 205 are insertable within and rotatably secured within the bore 2701 of the drive socket 2601.

Figure 18A:
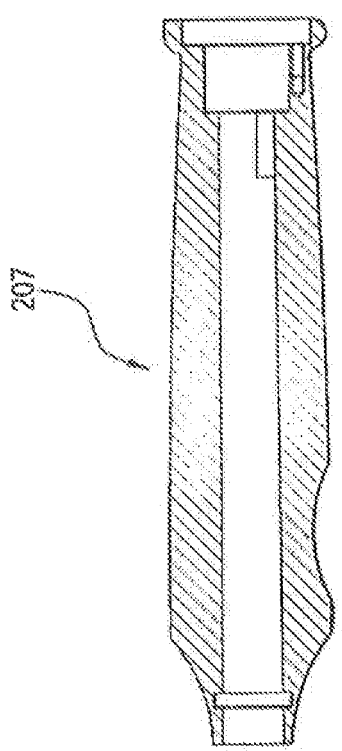
FIGS. 18A to 18C illustrate various views of the handle, according to an example embodiment of the present invention.
Figure 18C:
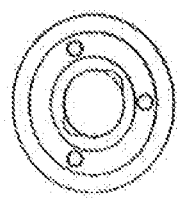
Figure 18B:
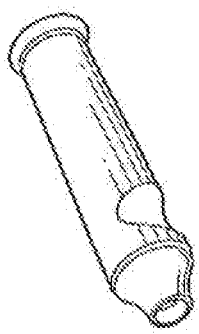

FIGS. 18A to 18C illustrate various views of the handle 207. When the flexible shaft extender 10 is assembled, the rotatable drive shafts 205 are positioned within the tubes 210, which may be made of a material, e.g., teflon, that minimizes the friction between the rotatable drive shafts 205 and the tubes 210.

In use, the quick connect collar 1603 is attached to the second coupling 185 at the distal end 180 of the flexible shaft 170. In this manner, the first connector 66 and the second connector 68 of the second coupling 185, that engage and are rotatably secured with first and second rotatable drive shafts 30 and 32, may also engage and be rotatably secured with the drive socket assembly 1612, which in turn engages and is rotatably secured with the proximal ends of the drive shafts 205.

In addition, a surgical attachment 190 may be attached to the distal tip assembly 201. In this manner, the distal ends of the drive shafts 205 may engage and be rotatably secured with complementary connectors of the surgical attachment 190. Rotation of the first and second rotatable drive shafts 30 and 32 of the flexible shaft 170 by the electro-mechanical driver device 110 cause the drive shafts 205 of the flexible shaft extender 10 to rotate, which thereby rotate the complementary connectors of the surgical attachment 190 so as to operate the surgical attachment 190. Furthermore, data, such as usage data, operating data, etc. may be conveyed between the surgical attachment 190 and the data transfer cable 38 of the flexible shaft 170, and from the memory unit 174 of the flexible shaft extender 10 to the data transfer cable 38 of the flexible shaft 170.

The flexible shaft extender 10 provides a substantially rigid device that may be inserted by a user into a surgical site. The flexible shaft extender 10 may provide a user with improved control of the surgical attachment 190, as compared to the use of, e.g., a surgical attachment 190, that is attached directly to, e.g., the flexible shaft 170. For instance, when a surgical attachment is attached to a conventional flexible shaft, the surgical attachment is typically manipulated and/or positioned within the patient's body by the user holding the flexible shaft at a location near to the surgical attachment. For surgical locations within the patient's body that are difficult to access, the user may be required to hold the flexible shaft at a substantial distance from its point of connection to the surgical attachment. However, the flexibility of the flexible shaft may hinder a user's ability to accurately position the surgical attachment within the body. This may be problematic when the position of the surgical attachment is well within the patient's body and the user is forced to hold the flexible shaft at a substantial distance from its point of connection to the surgical attachment. The resulting lack of accuracy in positioning and manipulating the surgical attachment may negatively impact the effectiveness of the surgical attachment in performing the surgical procedure. However, the present invention according to various embodiments thereof, provides a substantially rigid extender between the surgical attachment and the flexible shaft. In this manner, a surgical attachment may be manipulated and/or positioned within the patient's body by the user holding the extender. Thus, for any surgical locations within a patient's body, and particularly for those surgical locations that are difficult to access, the user may hold the extender at a substantial distance from its point of connection to the surgical attachment without the flexibility of the flexible shaft hindering the user's ability to accurately position the surgical attachment within the body. Even when the position of the surgical attachment is well within the patient's body and the user is forced to hold the extender at a substantial distance from its point of connection to the surgical attachment, the substantially rigid extender may enable improved control by the user of the surgical attachment when positioning or manipulating same. The resulting improvement of accuracy in positioning and manipulating the surgical attachment may improve the effectiveness of the surgical attachment in performing the surgical procedure.

Furthermore, the flexible shaft extender 10 may be autoclavable by virtue of the material with which it is constructed, as well as the sealing components that prevent moisture from entering the flexible shaft extender 10. When autoclavable, the flexible shaft extender may be re-used, e.g., for different patients, different types of surgical procedures and/or with different surgical attachments, thereby providing a significant cost savings relative to single-use devices.

Thus, the several aforementioned objects and advantages of the present invention are most effectively attained. Those skilled in the art will appreciate that numerous modifications of the exemplary embodiment described hereinabove may be made without departing from the spirit and scope of the invention. Although various exemplary embodiments of the present invention has been described and disclosed in detail herein, it should be understood that this invention is in no sense limited thereby.

What is claimed is:

1. An electro-mechanical surgical system, comprising:
   an electro-mechanical driver device including a flexible shaft including a pair of rotatable drive members extending along a length thereof; and
   an extender having:
      a proximal end including a handle having a handle cap assembly configured to detachably couple to a distal end of the flexible shaft, the handle cap assembly including:
         a handle cap including at least two orifices;
         a key plate; and
         a quick connect collar mounted to a proximal end of the handle cap and retained thereagainst by the key plate; and
      a distal end configured to be detachably coupled to a proximal end of a surgical attachment,
   wherein each orifice of the at least two orifices is configured to engage and rotatably secure to a corresponding one of the pair of rotatable drive members of the electro-mechanical driver device such that rotation of the pair of rotatable drive members causes at least two rotatable shafts of the extender to rotate thereby transmitting a force to the surgical attachment so as to operate the surgical attachment.

2. The electro-mechanical surgical system of claim 1, wherein the handle cap has at least one aperture at the proximal end thereof.

3. The electro-mechanical surgical system of claim 2, wherein a distal end of the key plate seats within the at least one aperture at the proximal end of the handle cap.

4. The electro-mechanical surgical system of claim 1, wherein the quick connect collar is configured to facilitate coupling and uncoupling the extender to the distal end of the flexible shaft.

5. The electro-mechanical surgical system of claim 1, wherein the key plate includes a corresponding pair of orifices that align with the at least two orifices of the handle cap.

6. The electro-mechanical surgical system of claim 1, further comprising a pair of drive sockets, each drive socket of the pair of drive sockets being rotatably retained within a corresponding one of the at least two orifices of the handle cap.

7. The electro-mechanical surgical system of claim 6, wherein each drive socket of the pair of drive sockets have mounted thereon:
   a bearing spacer,
   a sealing element and
   a bearing, wherein the bearing spacer, the sealing element, and the bearing are configured to rotatably retain each drive socket of the pair of drive sockets in the corresponding one of the at least two orifices of the handle cap.

8. The electro-mechanical surgical system of claim 7, wherein the sealing element of each drive socket of the pair of drive sockets and seal elements provided at the distal end of the extender prevent moisture from entering the extender to allow sterilization of the extender via an autoclave.

9. The electro-mechanical surgical system of claim 1, wherein the key plate includes at least one aperture defined therethrough that is configured to provide access for a wiring harness retained within the handle cap assembly.

10. The electro-mechanical surgical system of claim 9, wherein a proximal end of the wiring harness is accessible through the at least one aperture defined through the key plate and includes a connector for connection to a data transfer cable of the flexible shaft.

11. The electro-mechanical surgical system of claim 10, wherein a distal end of the wiring harness extends out of the distal end of the extender for communicating data from the surgical attachment to the data transfer cable of the flexible shaft.

12. The electro-mechanical surgical system of claim 1, wherein the surgical attachment is a surgical stapler-cutter.

13. The electro-mechanical surgical system of claim 1, wherein the extender is flexible.

14. An electro-mechanical surgical system, comprising:
   an electro-mechanical driver device including a pair of rotatable drive members projecting from a distal end thereof;
   an extender having:
      a proximal end including a handle having a handle cap assembly configured to detachably couple to the distal end of the electro-mechanical driver device, the handle cap assembly including:
         at least two orifices, each orifice of the at least two orifices configured to engage and rotatably secure to a corresponding one of the pair of rotatable drive members of the electro-mechanical driver device; and
         a pair of drive sockets, wherein each drive socket of the pair of drive sockets is rotatably retained within a corresponding one of the at least two orifices of the handle cap assembly, each drive socket of the pair of drive sockets having mounted thereon:
            a bearing spacer;
            a sealing element; and
            a bearing, wherein the bearing spacer, the sealing element, and the bearing are configured to rotatably retain each drive socket of the pair of drive sockets in the corresponding one of the at least two orifices; and
      a distal end configured to be detachably coupled to a proximal end of a surgical attachment, wherein a rotation of either of the pair of rotatable drive members causes a corresponding one of a pair of rotatable shafts of the extender to rotate thereby transmitting a force to the surgical attachment so as to operate the surgical attachment.

15. The electro-mechanical surgical system of claim 14, wherein the pair of shafts of the extender are rotatable shafts.

16. The electro-mechanical surgical system of claim 14, wherein the sealing element of each drive socket of the pair of drive sockets and seal elements provided at the distal end of the extender prevent moisture from entering the extender to allow sterilization of the extender via an autoclave.

17. The electro-mechanical surgical system of claim 14, wherein the surgical attachment is a surgical stapler-cutter.

\* \* \* \* \*